United States Patent
Agarwal et al.

(10) Patent No.: US 10,675,482 B2
(45) Date of Patent: Jun. 9, 2020

(54) DEVICE AND METHOD FOR USE OF PHOTODYNAMIC THERAPY

(71) Applicant: CranioVation, Inc., Oakdale, MN (US)

(72) Inventors: Vijay Agarwal, Durham, NC (US); Ranjith Babu, Durham, NC (US); Jack Ratcliffe, Wendell, NC (US)

(73) Assignee: Craniovation, Inc., Oakdale, MN (US)

( * ) Notice: Subject to any disclaimer, the term of this patent is extended or adjusted under 35 U.S.C. 154(b) by 0 days.

(21) Appl. No.: 15/109,506

(22) PCT Filed: Jan. 2, 2015

(86) PCT No.: PCT/US2015/010053
§ 371 (c)(1),
(2) Date: Jul. 1, 2016

(87) PCT Pub. No.: WO2015/103484
PCT Pub. Date: Jul. 9, 2015

(65) Prior Publication Data
US 2016/0325110 A1 Nov. 10, 2016

Related U.S. Application Data

(60) Provisional application No. 61/923,639, filed on Jan. 4, 2014.

(51) Int. Cl.
*A61N 5/06* (2006.01)
*A61K 41/00* (2020.01)
(Continued)

(52) U.S. Cl.
CPC ............. *A61N 5/062* (2013.01); *A61B 90/10* (2016.02); *A61B 90/39* (2016.02);
(Continued)

(58) Field of Classification Search
CPC .............. A61N 5/062; A61N 5/0601; A61N 2005/0612; A61N 2005/063;
(Continued)

(56) References Cited

U.S. PATENT DOCUMENTS 4,576,177 A * 3/1986 Webster, Jr. ......... A61B 8/0833
600/439
4,735,201 A * 4/1988 O'Reilly ................ A61B 18/28
606/28
(Continued)

FOREIGN PATENT DOCUMENTS

CN 101022852 A 8/2007
CN 101228460 A 7/2008
(Continued)

OTHER PUBLICATIONS

Agarwal, V., International Patent Application No. PCT/US2015/010053, International Search Report and Written Opinion, dated May 4, 2015.
(Continued)

*Primary Examiner* — Michael W Kahelin
*Assistant Examiner* — Vynn V Huh
(74) *Attorney, Agent, or Firm* — K&L Gates LLP (57) ABSTRACT

An intracranial treatment apparatus comprises an outer shaft having a proximal end and a distal end for positioning within the tissue region of the brain. The outer shaft defines a lumen extending between the proximal end and the distal end of the outer shaft and having at least one aperture adjacent the distal end of the outer shaft. An inner light-delivery element having a distal end and a proximal end is adapted to be operatively connected to the light source. The light-delivery element is configured to be received within the lumen and extend from the proximal end of the shaft to adjacent the distal end of the shaft. The light-delivery element is adapted (Continued)

to deliver light from the light source through the at least one aperture of the outer shaft to the tissue region of the brain in proximity to the distal end of the outer shaft.

20 Claims, 10 Drawing Sheets

(51) Int. Cl.
    *A61B 90/00*     (2016.01)
    *A61B 90/10*     (2016.01)
    *A61B 18/22*     (2006.01)
    *A61B 18/00*     (2006.01)

(52) U.S. Cl.
    CPC ........ *A61K 41/0057* (2013.01); *A61N 5/0601* (2013.01); *A61B 2018/00321* (2013.01); *A61B 2018/2261* (2013.01); *A61B 2018/2266* (2013.01); *A61B 2018/2272* (2013.01); *A61B 2090/3954* (2016.02); *A61B 2090/3966* (2016.02); *A61N 2005/063* (2013.01); *A61N 2005/0612* (2013.01); *A61N 2005/0651* (2013.01); *A61N 2005/0665* (2013.01)

(58) Field of Classification Search
    CPC .... A61N 2005/0651; A61N 2005/0665; A61B 90/39; A61B 18/22; A61B 2090/3954; A61B 2090/3966; A61K 41/0057
    USPC ...................................... 606/2–19
    See application file for complete search history.

(56) References Cited

U.S. PATENT DOCUMENTS

| | | | |
|---|---|---|---|
| 6,572,839 B2 | 6/2003 | Sugita et al. | |
| 6,576,257 B1 | 6/2003 | Yarmut | |
| 6,622,049 B2 | 9/2003 | Penner et al. | |
| 6,723,750 B2 | 4/2004 | Voet | |
| 7,018,395 B2 | 3/2006 | Chen | |
| 7,252,677 B2 | 8/2007 | Burwell et al. | |
| 7,514,069 B2 | 4/2009 | Achilefu et al. | |
| 7,790,144 B2 | 9/2010 | Achilefu et al. | |
| 8,070,682 B2 | 12/2011 | Zhu | |
| 8,123,789 B2 | 2/2012 | Khanna | |
| 8,206,326 B2 | 6/2012 | Schafer et al. | |
| 8,318,133 B2 | 11/2012 | Achilefu et al. | |
| 8,548,562 B2 | 10/2013 | Trachtenberg et al. | |
| 8,574,174 B2 | 11/2013 | Schafer et al. | |
| 8,741,262 B2 | 6/2014 | Ni et al. | |
| 8,758,725 B2 | 6/2014 | Sharma et al. | |
| 8,771,741 B2 | 7/2014 | Adair et al. | |
| 8,979,775 B2 | 3/2015 | Schafer et al. | |
| 9,023,090 B2 | 5/2015 | Palti | |
| 9,072,774 B2 | 7/2015 | Zheng et al. | |
| 9,313,423 B2 | 4/2016 | Wang et al. | |
| 9,371,555 B2 | 6/2016 | Roberts | |
| 9,463,256 B2 | 10/2016 | Lub et al. | |
| 9,475,028 B2 | 10/2016 | Krishna et al. | |
| 9,492,121 B2 | 11/2016 | Andrews et al. | |
| 9,492,681 B2 | 11/2016 | Aydt et al. | |
| 9,498,650 B2 | 11/2016 | Schafer et al. | |
| 9,510,909 B2 | 12/2016 | Grant et al. | |
| 9,572,880 B2 | 2/2017 | Harris et al. | |
| 2003/0114434 A1 | 6/2003 | Chen et al. | |
| 2004/0171601 A1 | 9/2004 | Fukumura et al. | |
| 2007/0005121 A1 | 1/2007 | Khanna | |
| 2007/0260295 A1* | 11/2007 | Chen ................... | A61N 5/0601 607/88 |
| 2010/0262115 A1 | 10/2010 | Madiyalakan et al. | |
| 2012/0016429 A1 | 1/2012 | Klorg | |
| 2012/0089205 A1 | 4/2012 | Boyden et al. | |

FOREIGN PATENT DOCUMENTS

| | | | | |
|---|---|---|---|---|
| CN | 102885648 A | 1/2013 | | |
| EP | 1909908 B1 | 3/2011 | | |
| JP | S60-053161 A | 3/1985 | | |
| JP | S62-202813 U | 12/1987 | | |
| JP | 2003503103 A | 1/2003 | | |
| JP | 2005-125075 A | 5/2005 | | |
| JP | 2005152093 A | 6/2005 | | |
| JP | 2011-509737 A | 3/2011 | | |
| WO | WO 9210142 A1 * | 6/1992 | ........... | A61N 5/0601 |
| WO | 9505214 A1 | 2/1995 | | |
| WO | WO 9505214 A1 * | 2/1995 | ........... | A61N 5/0601 |
| WO | 9628200 A1 | 9/1996 | | |
| WO | 2009095912 A1 | 8/2009 | | |

OTHER PUBLICATIONS

USPTO; Office Action for U.S. Appl. No. 15/447,185 dated Jun. 15, 2017, 26 pages.
USPTO; Final Office Action for U.S. Appl. No. 15/447,185 dated Nov. 29, 2017, 28 pages.
European Patent Application No. 18191185.0, Extended European Search Report dated Oct. 17, 2018, 8 pages.

* cited by examiner

DEVICE AND METHOD FOR USE OF PHOTODYNAMIC THERAPY

BACKGROUND

A device and method is shown and described for use in irradiating or otherwise administering light to a location within the body of a patient and, more particularly, a device and method for the use of photodynamic therapy for the therapeutic treatment of tissue in the brain or other part of the body of the patient, including tumors, such as malignant brain neoplasms.

There are a variety of medical procedures that require light or irradiated energy to be administered to a patient within the body. Photodynamic therapy (PDT) is a form of treatment that relies on exposing an area of tissue to a selected wavelength of activating radiation. PDT uses non-toxic, photosensitive compounds that accumulate selectively in targeted tissue. The photosensitive compounds become toxic when exposed to light at selected wavelengths. This leads to chemical destruction of any tissues which have selectively taken up the photosensitizer and have been selectively exposed to light.

One application of PDT is in oncology for the destruction of malignant cell masses in the body. PDT has been used effectively in the treatment of a variety of human tumors and precancerous conditions, including basal and squamous cells, skin cancers, lung cancer, breast cancer, metastatic to skin, brain tumors, and head and neck, stomach, and the female genital tract malignancies. PDT has also been used to treat the cancers and precancerous conditions of the esophagus, such as Barrett's esophagus. In the latter application, a photosensitizer, such as Photophrin, is first administered. A 630 nm light from a KTP/dye laser, a diode laser, or an argon-pumped dye-laser is delivered using a PDT balloon having a reflective inner surface. The PDT balloon includes an internal cylindrical diffuser and has several windows for illuminating the treatment area.

Therapeutic use of PDT in the brain has been minimal Therefore, evidence for the efficacy and the safety of PDT for use in the brain is limited in quality and quantity. However, the introduction of probes or similar devices into the brain is common in many surgical procedures. The probes used for intracranial penetration are typically fabricated so that their introduction into the brain is as minimally traumatic as possible. During typical implantation, a surgeon feeds the probe into the brain through an aperture in the skull. Probes inserted into the brain typically include ports for drug delivery or paired contacts positioned at specific points or regions in the brain. The contacts are electrical, chemical, electrochemical, temperature or pressure contacts, which enable the observation and analysis of the brain state or provide stimulation. In addition, neurosurgeons use photosensitizers when resecting infiltrative tumors. The photosensitizers fluoresce when light of a certain wavelength is shined on the cells allowing for rough identification of the tumor margins.

For the foregoing reasons, there is a need for a new device and method for the use of photodynamic therapy (PDT) for the therapeutic treatment of tissue in the brain of a patient. The new device and method should ideally include a probe or similar device familiar to neurosurgeons to deliver PDT for the treatment of the brain tissue, including tumors such as malignant brain neoplasms. In one aspect, the new device and method for PDT is useful and effective for other parts of the body in addition to the brain.

SUMMARY

An apparatus for use in photodynamic therapy is described, in one embodiment, for intracranial treatment of a tissue region of a brain of a patient. The intracranial treatment apparatus comprises an outer shaft having a proximal end and a distal end for positioning within the tissue region of the brain. The outer shaft defines a lumen extending between the proximal end and the distal end of the outer shaft and having at least one aperture adjacent the distal end of the outer shaft. An inner light-delivery element has a distal end and a proximal end adapted to be operatively connected to a light source. The light-delivery element is configured to be received within the lumen and extend from the proximal end of the shaft to adjacent the distal end of the shaft. The light-delivery element is adapted to deliver light from the light source through the at least one aperture of the outer shaft to the tissue region of the brain in proximity to the distal end of the outer shaft.

In one aspect, the outer shaft has a plurality of ports radially or axially spaced along the outer shaft. In this embodiment, the light-delivery element comprises a plurality of independently movable fiber optic cables, each of the plurality of fiber optic cables extending from one of the ports and axially movable within the lumen relative to the outer shaft between a first position where the distal end of the fiber optic cable is adjacent the outer shaft, and a second position where the distal end of the fiber optic cable extends into the tissue region of the brain in proximity to the outer shaft.

A method for intracranial treatment of a tissue region of a brain of a patient is also described. The intracranial treatment method comprises the steps of providing a device including a light source for selectively irradiating tissue. The irradiating device comprises an outer shaft having a proximal end and a distal end for positioning within the tissue region of the brain. The outer shaft defines a lumen extending between the proximal end and the distal end of the outer shaft and having at least one aperture adjacent the distal end of the outer shaft. An inner light-delivery element has a distal end and a proximal end configured to be operatively connected to the light source. The light-delivery element is configured to be received within the lumen and extend from the proximal end of the outer shaft to adjacent the distal end of the outer shaft. The distal end of the outer shaft is positioned within close proximity to a selected site adjacent the tissue region in the brain. Light is delivered from the light source through the light-delivery element and the at least one aperture of the outer shaft to the tissue region of the brain in proximity to the distal end of the outer shaft sufficient to kill a portion of the tissue.

In a further aspect of the method, the outer shaft has a plurality of ports radially or axially spaced along the outer shaft. The light-delivery element comprises a plurality of independently movable fiber optic cables, each of the plurality of fiber optic cables extending from one of the ports and axially movable within the lumen relative to the outer shaft between a first position where the distal end of the fiber optic cable is adjacent the outer shaft, and a second position where the distal end of the fiber optic cable extends into the tissue region of the brain in proximity to the outer shaft. The positioning step comprises moving the plurality of fiber optic cables to the second position such that the distal end of each of the plurality of fiber optic cables extends through the port of the outer shaft and into the tissue region in proximity to the outer shaft when the plurality of fiber optic cables is advanced distally relative to the lumen.

BRIEF DESCRIPTION OF THE DRAWINGS

For a more complete understanding of the present invention, reference should now be had to the embodiments shown in the accompanying drawings and described below. In the drawings.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

As used herein, the term "light", "light irradiation", or "irradiation" refers to light of wavelengths from about 300 nm to about 1200 nm. This includes UV, visible and infrared light. The PDT device can be used with any wavelength of light. The choice of wavelength will be determined by the intended application, namely being selected to match the activation wavelength of the photosensitive drug or the wavelength used for irradiation when a photo-activated compound is not employed.

Figure 1:
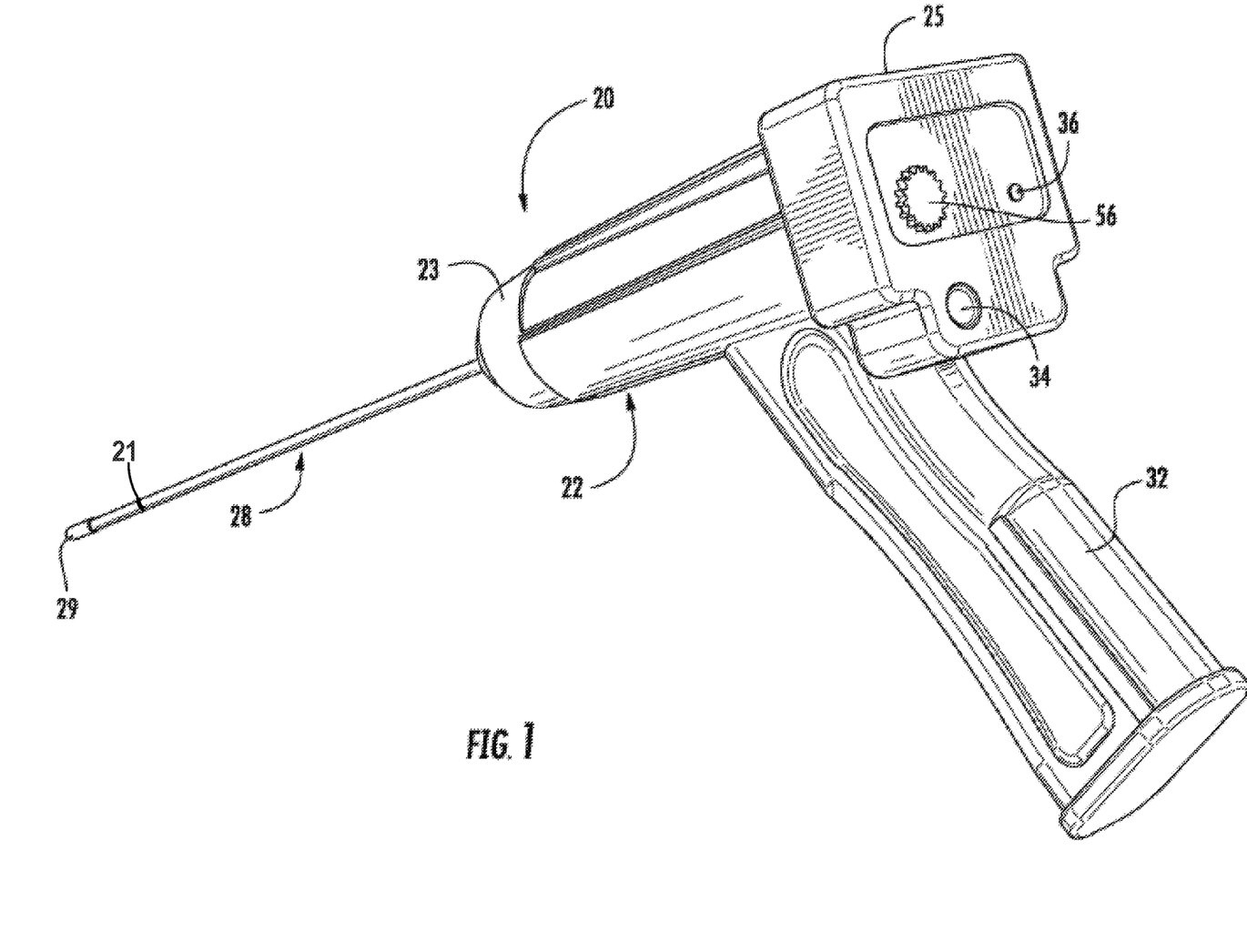
FIG. 1 is a perspective view of an embodiment of a device for providing photodynamic therapy to the brain of a patient.
Figure 2:
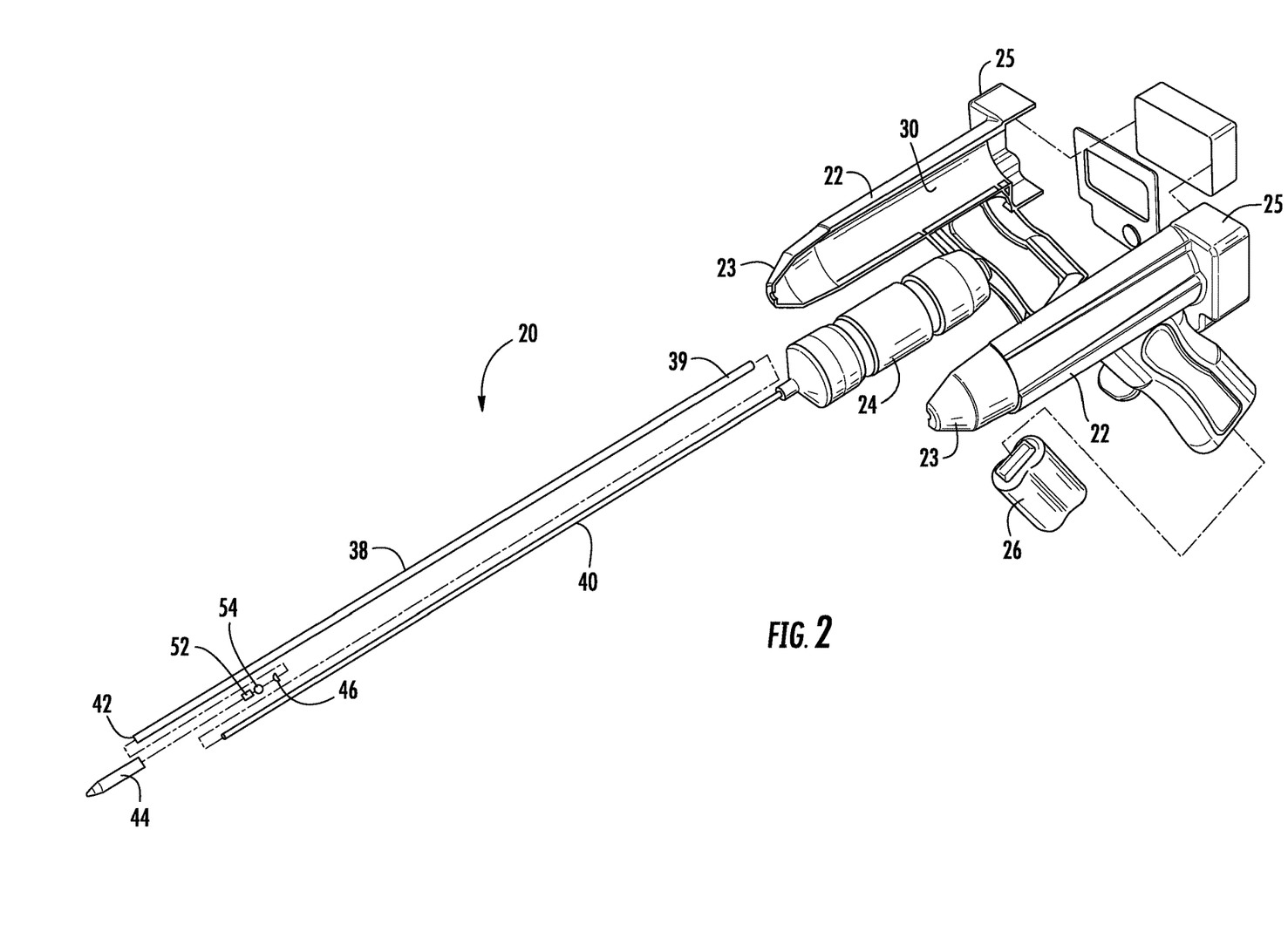
FIG. 2 is exploded perspective of the photodynamic therapy device as shown in FIG. 1.
Figure 3:
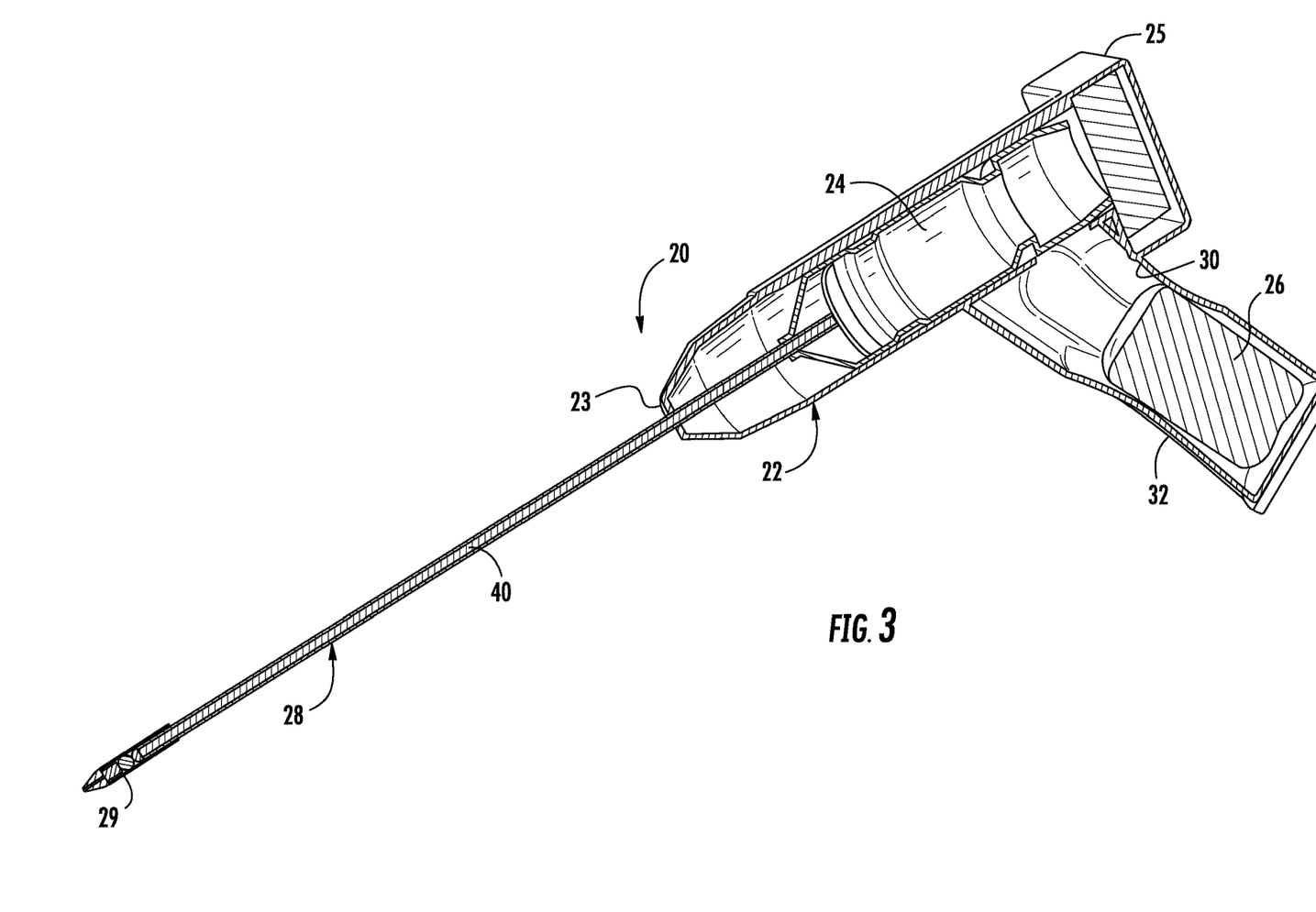
FIG. 3 is a longitudinal cross-section view of the photodynamic therapy device as shown in FIG. 1.

Referring now to the FIGS. 1-3, wherein like reference numerals designate corresponding or similar elements throughout the several views, an embodiment of a device for selectively applying photodynamic therapy to structures in the brain is shown in FIGS. 1-3 and generally designated at 20. The PDT device 20 comprises a housing 22 that accommodates a light-generating apparatus, including a light source 24 and a power source 26 to power the light source. A tubular wand 28 extends from a distal end 23 of the housing 22. A embodiment of a method of photodynamic therapy comprises positioning the wand 28 of the PDT device 20 adjacent to the target site so that the wand is brought into at least partial contact, or close proximity, with a tissue structure within the patient's brain, such as tumor tissue. Light is then delivered via the wand 28 for treating at least a portion of the tissue structure in situ. The PDT device 20 is particularly useful for therapeutic treatment of benign or malignant tumors in the brain.

The housing 22 may be formed from a plastic material that is molded into a suitable shape for handling by a surgeon. As shown in FIGS. 2 and 3, the housing 22 defines an inner cavity 30 for receiving the light source 24 and the power supply 26 and associated electrical connections (not shown). In this embodiment of the PDT device 20, a proximal handle 32 is integral to the housing 22. The handle 32 is sized to be grasped and manipulated by the surgeon during a surgical procedure. It is understood that the housing 22 of the PDT device 20 may be various sizes and shapes, depending upon the context of use. As best seen in FIG. 1, the proximal end 25 of the housing 22 includes an actuating button 34 for selectively powering the light source 24. An indicator light 36 shows when the light source 24 is powered. The power source 26 provides a sufficient voltage to establish the requisite conditions for light delivery to the tissue. In the embodiment shown, the power supply 26 is an onboard battery, for example, a rechargeable 11.1 V lithium ion battery.

The tubular wand 28 comprises an outer shaft 38 defining a lumen extending from the proximal end 39 of the shaft to the distal end 42 of the shaft 38. A fiber optic cable 40 is disposed within the lumen and operates to transfer light from the light source 24 to distal end 29 of the wand. The light is emitted from the distal end 29 of the wand 28 for exposing a tissue region in the brain of a patient. The outer shaft 38 is a thin elongated tubular element with a smooth outer surface in order to minimize the amount of brain tissue contacted and to minimize damage to contacted brain tissue. The outer shaft 38 will typically have a diameter of at least about 0.6 mm and frequently in the range from about mm 1 to about 10 mm. In one embodiment, the diameter of the outer shaft 38 is preferably between and 1.5 millimeters, most preferably about 1.0 millimeter. The outer shaft 38 generally has a length dimension which permits the shaft 38 to be introduced through a burr hole in the cranium or through a conventional transoral or transphenoidal route. Thus, the outer shaft 38 will typically have a length of at least about 5 cm for open surgical procedures and at least about 10 cm, or more typically about 20 cm or longer for endoscopic procedures.

The outer shaft 38 is preferably rigid for percutaneous, transluminal or direct delivery to the brain in either open procedures or port access type procedures. The outer shaft 38 may be formed from polyurethane, silicone, polyimede, or other biocompatible material. Alternatively, the shaft may comprise a metal, which is selected from the group consisting of tungsten, stainless steel alloys, platinum or its alloys, titanium or its alloys, molybdenum or its alloys, and nickel or its alloys. Alternatively, the outer shaft 38 may be flexible, being combined with a generally rigid internal tube (not shown) for mechanical support. Flexible shafts may also be combined with pull wires for guiding the outer shaft 38 to a target tissue site, shape memory actuators, and other known mechanisms for effecting selective deflection of the outer shaft to facilitate positioning of a distal end 39 of the shaft 38. The outer shaft 38 may also include elements for providing a location marker for determining the precise position of the wand 28 within the brain of a patient.

The fiber optic cable 40 may be a fiber optic bundle or liquid light guide. For convenience, these elements hereinafter are referred to collectively as a fiber optic cable 40. The fiber optic cable 40 extends from the proximal end 39 to the distal end 42 of the outer shaft 38. The proximal end of the fiber optic cable 40 is operably connected to the light source 24 for delivering light to a tissue region adjacent the distal end 42 of the shaft 38. The fiber optic cable 40 can be of any diameter so long as the fiber optic cable can be inserted into the lumen of the outer shaft 38. The preferred diameter of the fiber optic cable is from about 50 microns to about 1000 microns and preferably about 400 microns. The choice of the diameter will depend on the brightness of the light source 24 and the optical power output required from the tip of the fiber optic cable 40.

Figure 4:
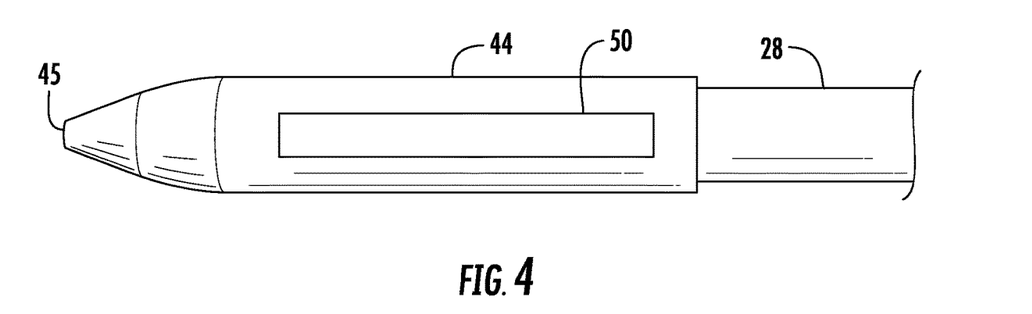
FIG. 4 is a close-up view of an embodiment of tip of a wand for use with the photodynamic therapy device as shown in FIG. 1.
Figure 5:
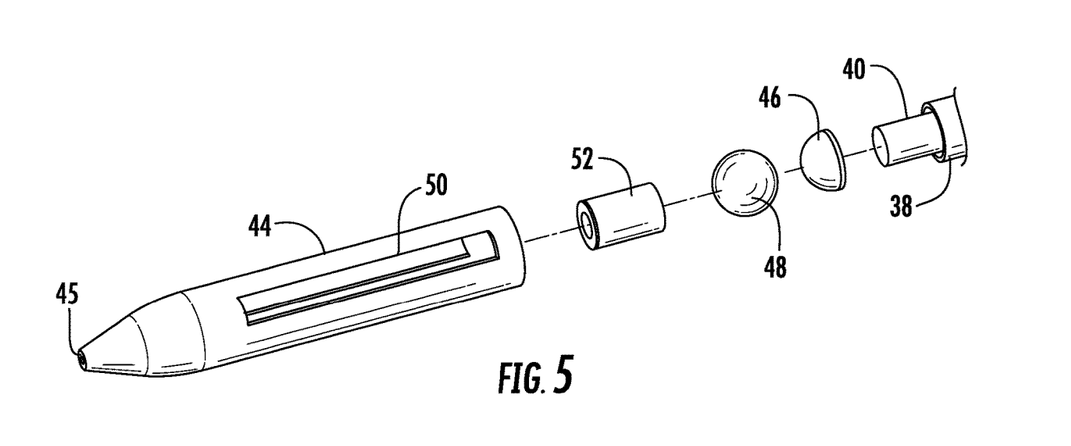
FIG. 5 is an exploded perspective view of the tip of the wand as shown in FIG. 4.
Figure 6:
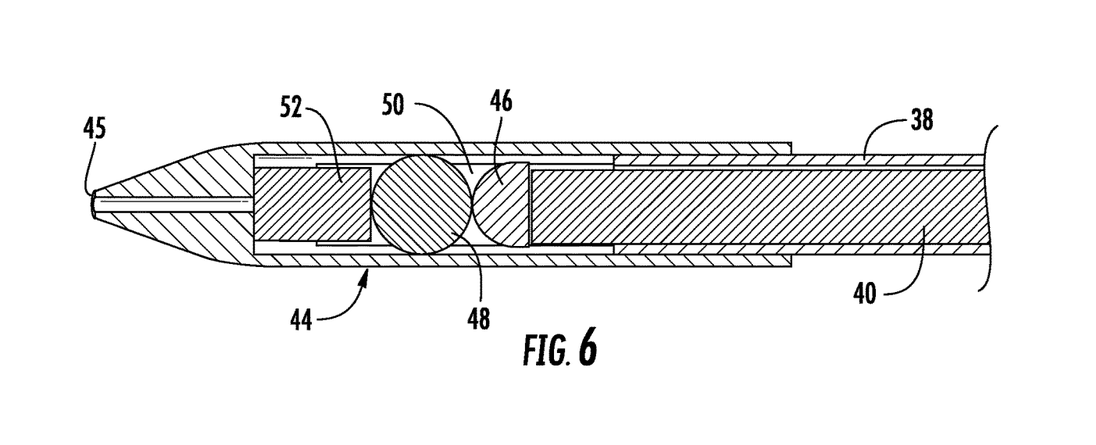
FIG. 6 is a longitudinal cross-section view of the tip of the wand as shown in FIG. 4.

Referring to FIGS. 4-6, the distal end 29 of the wand 28 comprises a rigid elongated end cap 44 coupled to the distal end 42 of the outer shaft 38. The end cap 44 is generally cylindrical and extends from the distal end 42 of the shaft 38 a distance of about 1 mm to about 20 mm. The end cap 44 tapers to a point 45 at a closed distal end. The end cap houses a diffusion tip or diffuser 46 and a ball bearing 48. As used herein, a diffuser or diffusion tip, is defined as an element that can be attached to the end of a fiber optic cable, or a structure that can be formed at the end of the fiber optic cable, that provides a means for diffusing (scattering) the light being transmitted through the fiber optic cable so that it radiates outward from the fiber. In the embodiment shown in the FIGs., the diffuser 46 is a generally hemispherical reflective shell that mounts to the distal end of the fiber optic cable 40 which is received within the shell. Light transmitted and emitting from the fiber optic cable 40 is diffused by the diffuser 46 for providing an even radial distribution of the light. A diffuse source of radiation can expose a greater area of tissue to activation energy. The outer surface of the ball bearing 48 is reflective to further diffuse the transmitted light.

One or more apertures 50 are provided along the surface of the end cap 44. For example, the embodiment shown in FIGS. 4-6 shows a pair of opposed axial apertures 50 circumferentially spaced on the body of the end cap 44. During PDT, light is delivered to the surrounding brain tissue region through the apertures 50. The end cap 44 may also contain a right angle prism to provide for re-direction of light through the apertures 50. The fiber optic probe 40 is arranged to the right angle prism so that the light exits from the apertures 50 in the end cap 44.

An optional piezoelectric ceramic member 52 may also be housed within the end cap 44. The piezoelectric member 52 is coupled to wire connectors 54 that extend to the proximal end of outer shaft 38 where they are suitably connected to the power supply 26. A frequency level adjustment knob 66 on the housing 22 enables adjustment of the intensity of the piezoelectric member 52 allowing for variable intensity application of a desired frequency.

Figure 9:
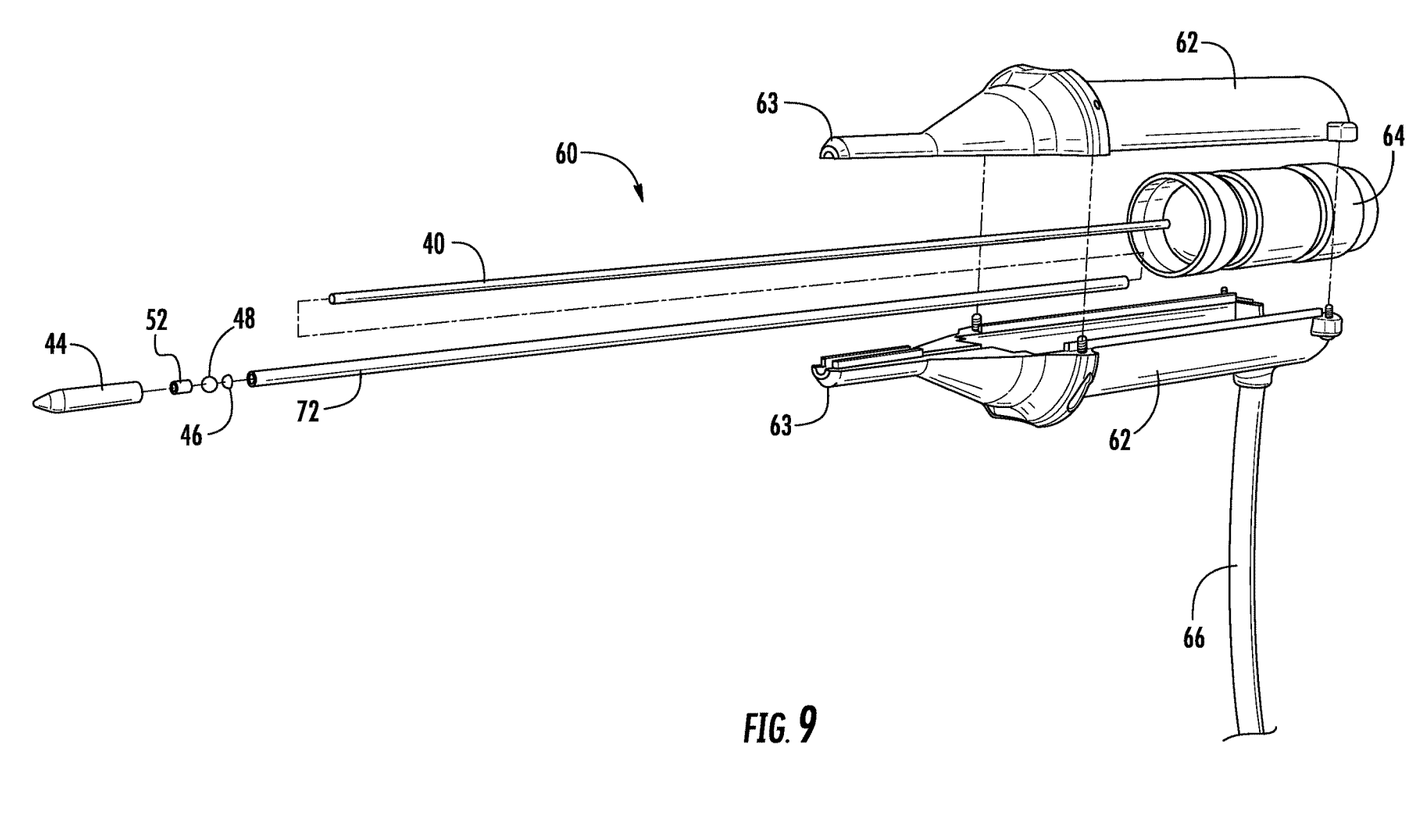
FIG. 9 is an exploded perspective view of the photodynamic therapy device as shown in FIGS. 7 and 8.
Figure 10:
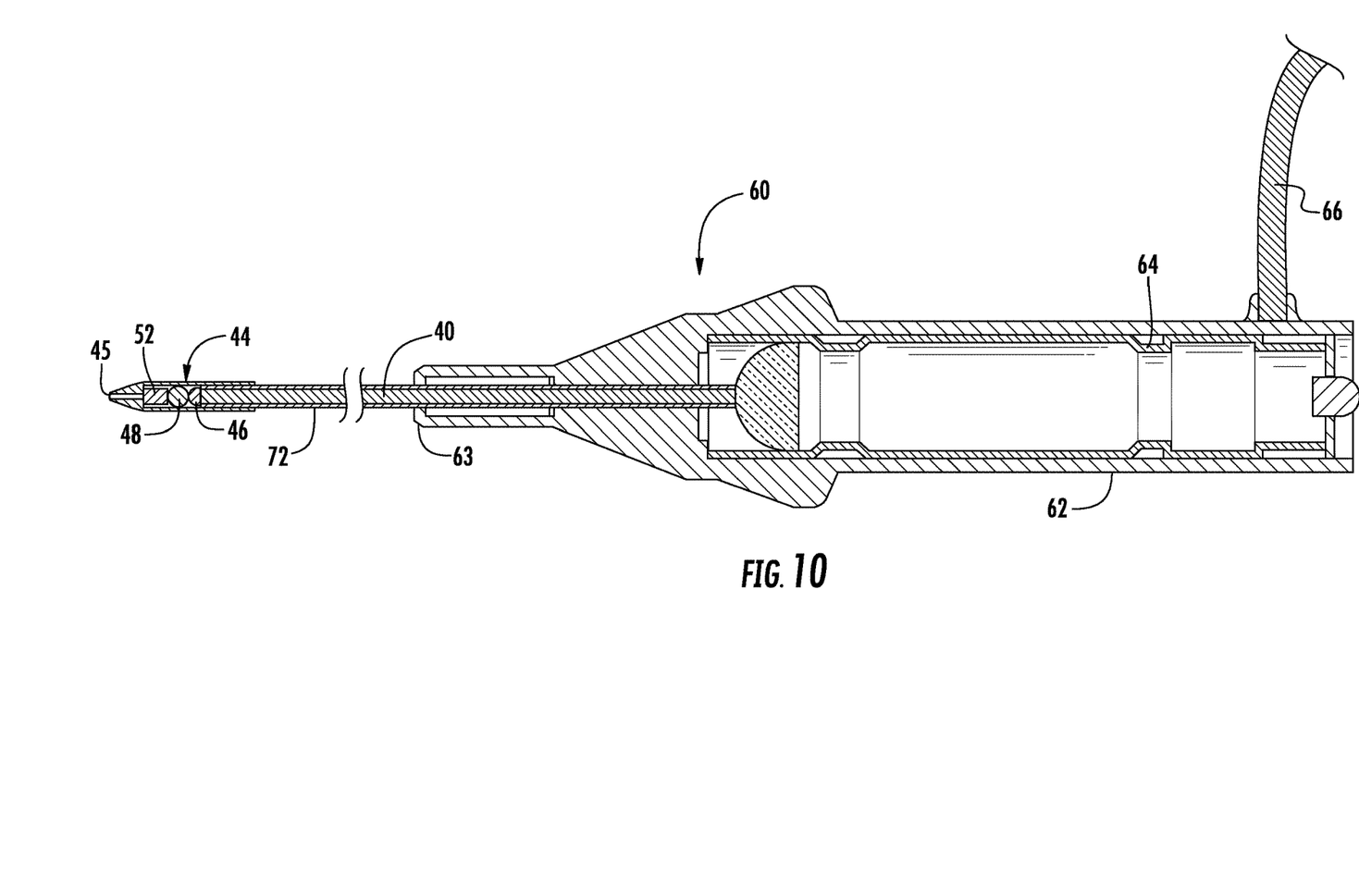
FIG. 10 is a longitudinal cross-section of the photodynamic therapy device as shown in FIGS. 7 and 8.

Referring now to the FIGS. 7-10, another embodiment of a device for selectively applying photodynamic therapy to structures in the brain is shown and generally designated at 60. The PDT device 60 comprises a housing 62 that accommodates a light source 64. The housing provides a suitable interface for receiving an electrical connecting cable 66 from a power source (not shown) for providing power to the light source 64. A tubular wand 66 extends from a distal end 63 of the housing 62 which tapers to conform to a proximal end 67 of the wand 66. As shown in FIGS. 9 and 10, the housing 62 defines an inner cavity 70 that houses the light source 64 and associated electrical connections (not shown). The housing 62 may be formed from a plastic material that is molded into a suitable shape for handling by a surgeon. The housing 62 of the PDT device 60 is sized to be grasped and manipulated by the surgeon during a surgical procedure.

The tubular wand 68 comprises an elongated outer shaft 72 defining a lumen extending from a proximal end 73 of the shaft 72 to a distal end 74 of the shaft 72. A plurality of fiber optic cables 76 are disposed within the lumen and operate to transfer light from the light source 64. The diameter of the outer shaft is preferably in the range from about 0.08 mm to about 1.0 mm, and more preferably in the range of from about 0.05 mm to about 0.4 mm. The outer shaft 72 extends about 1 cm to about 20 cm from the distal end 63 of the housing 62. In this embodiment of the PDT device 60, the outer shaft 72 may assume a wide variety of configurations, with the primary purpose being to mechanically support a plurality of light-delivering elements and permit the surgeon to manipulate the light delivery elements from the proximal end of the housing 62. The shaft may be formed from the group including stainless steel, copper-based alloys, titanium or its alloys, and nickel-based alloys.

Each of the fiber optic cables 76 has a proximal end and a distal end. The proximal portion of outer shaft 72 includes a multi-fitment (not shown) which provides for interconnections between the proximal ends of the fiber optic cables 76 and the light source 64 within the housing 62 adjacent to the fitment. In one embodiment, the fiber optic cables 76 are independent from one another and deliver light separately from the light source 64. Alternatively, the fiber optic cables 76 may be connected together at their the proximal ends to form a single fiber that couples to the light source 64. It is understood that the PDT device 60 is not limited to isolated fiber optic cables or even to a plurality of fiber optic cables. For example, the plurality of fiber optic cables 76 may be connected to a single lead that extends through the outer shaft 72 to the light source 64.

Figure 11:
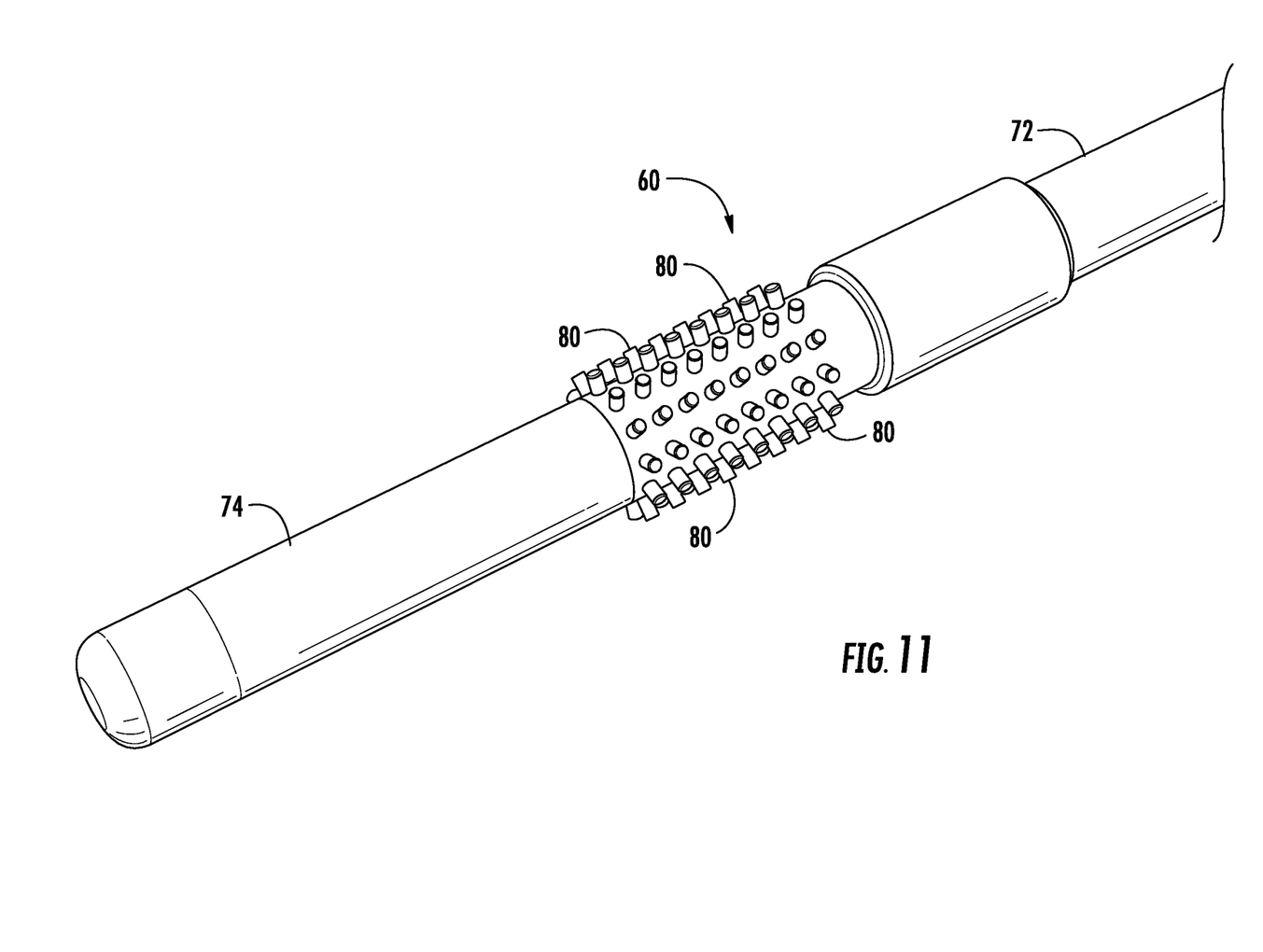
FIG. 11 is a close-up perspective view of an embodiment of tip of a wand for use with the photodynamic therapy device as shown in FIGS. 7 and 8 and showing with light delivering elements in a first position.
Figure 12:
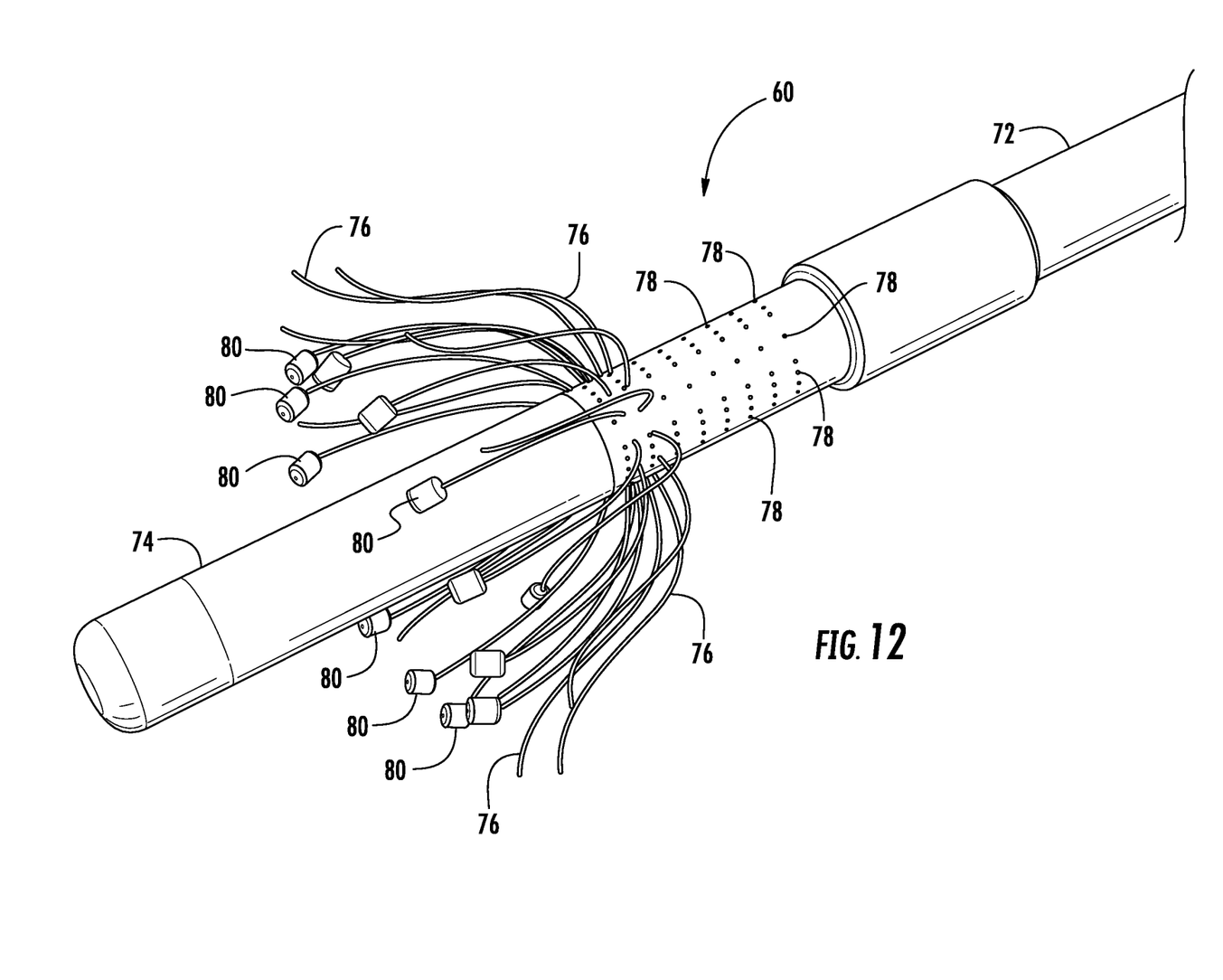
FIG. 12 is a close-up perspective view of the tip of the wand as shown in FIG. 11 with light delivering elements in a second position.

Referring to FIGS. 11-13, the outer shaft 72 defines a plurality of axially and circumferentially spaced ports 78 adjacent the distal end 74 of the shaft 72. The posts 78 open into the lumen and are each configured for passing one of the plurality of fiber optic cables 76 running axially through the lumen. Each of the fiber optic cables 76 has a distal end which passes from the lumen via a corresponding port 78 into the tissue region beyond the surface of the outer shaft 72.

A light-emitting diode (LED) 80 is connected to the distal end of each of the fiber optic cables 76 external to the outer shaft 72. In this arrangement, the PDT device 60 comprises a distributed array of LED's 80 spaced axially and circumferentially around the distal end 74 of the outer shaft 72. LED's 80 emit a diverging beam of light without the need for a diffuser. In addition, while the LED's 80 are depicted as short cylinders, the LED's 80 can have any suitable shape, including spherical, twizzle shapes for needle-like cutting, spring shapes or other twisted metal shapes, and the like. The fiber optic cables 76 have a length greater than the shaft length and are configured for axial movement relative to the shaft. It is understood that the assembly can include many fiber optic cables 76 of different lengths and having different arrangements of apertures or ports to selectively provide for treatment of specific desired targeted tissue regions in the brain. Optic exit site and depth of penetration can be determined preoperatively via 3-dimensional imaging planning software. The area of the tissue treatment can vary widely, with particular areas and geometries being selected for specific applications. This allows for optimal fiber optic penetration into, for example, a tumor, which also optimizes the amount of light that is delivered to the tumor.

Figure 7:
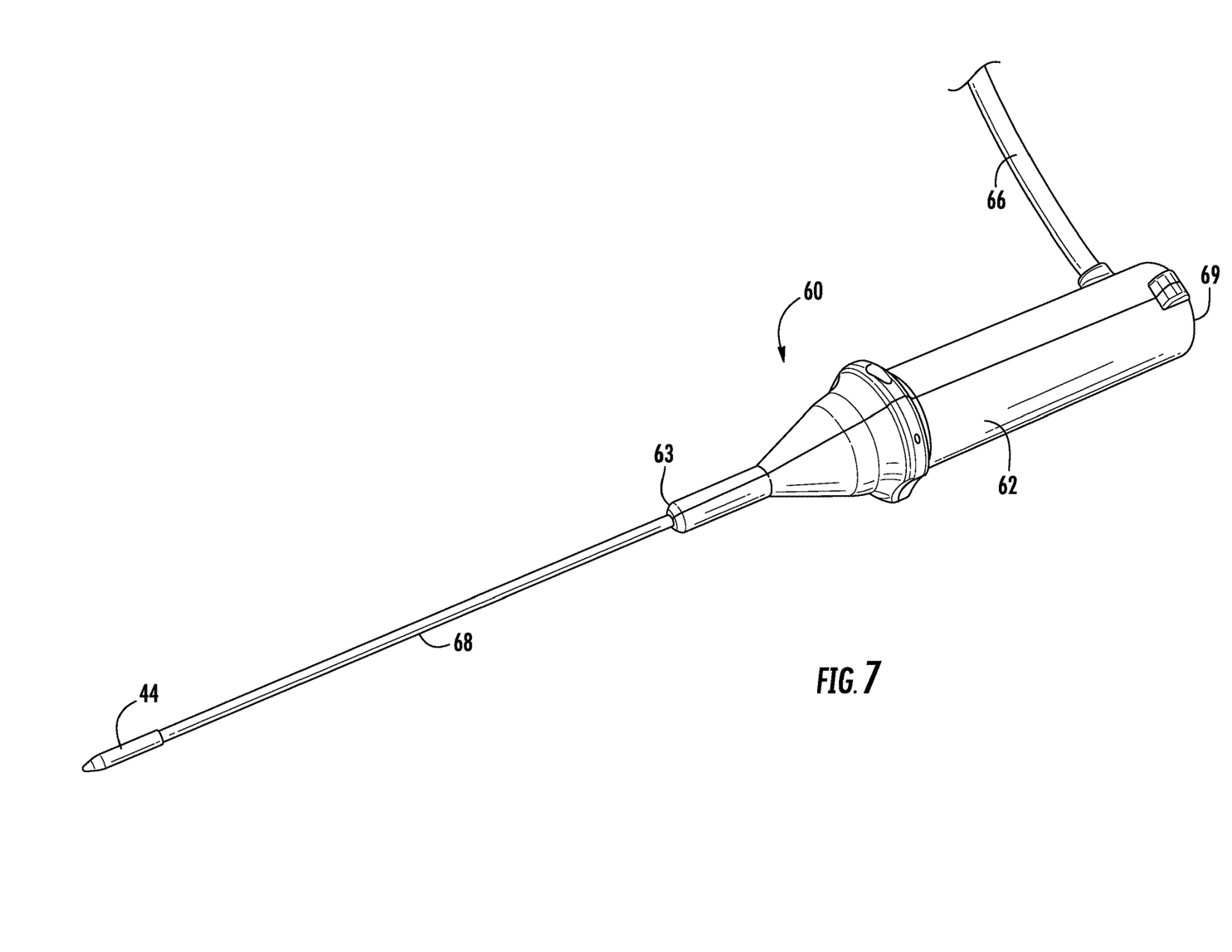
FIG. 7 is front perspective view of another embodiment of a device for providing photodynamic therapy to the brain of a patient.
Figure 8:
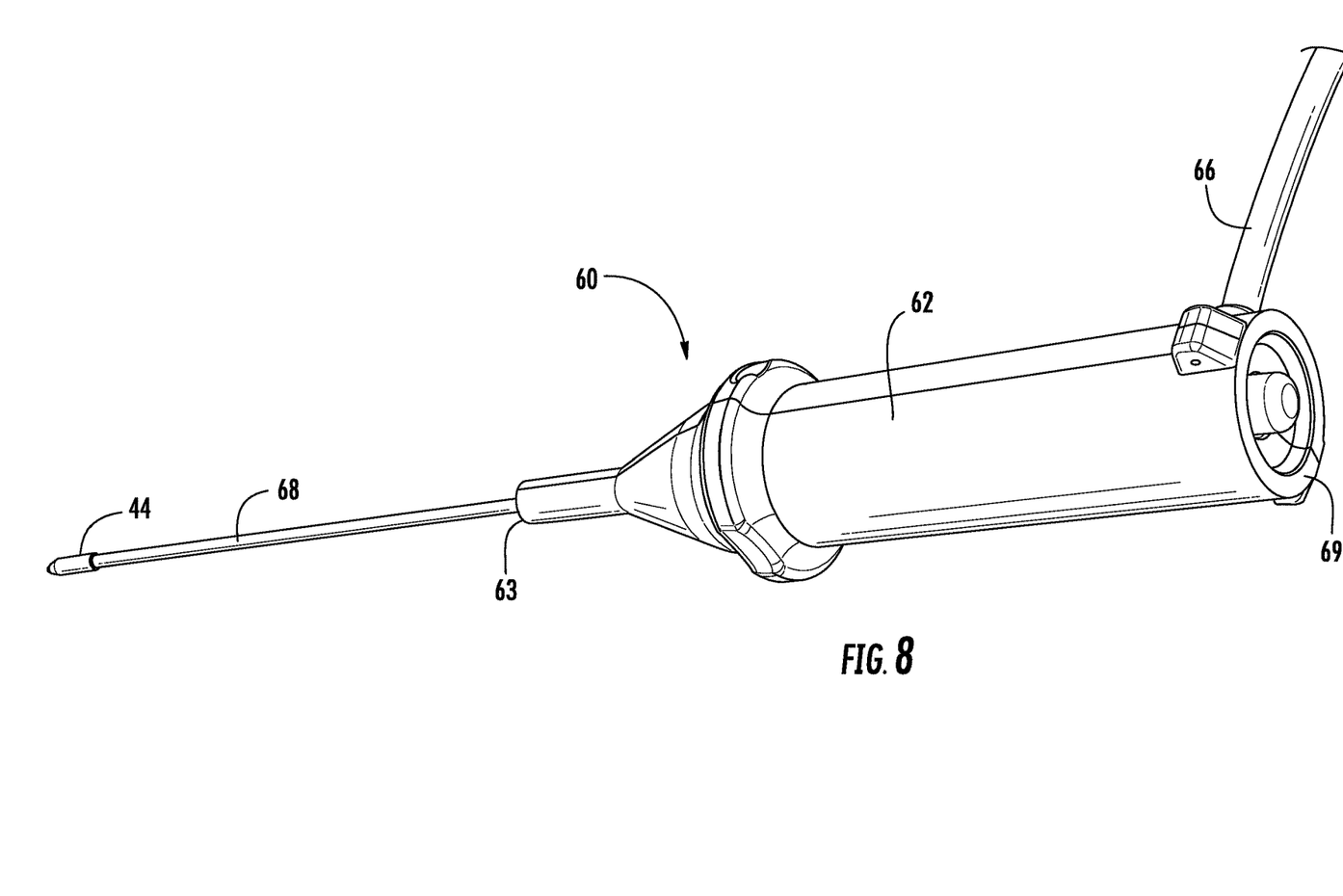
FIG. 8 is a rear perspective view of the photodynamic therapy device as shown in FIG. 7.

In use, the wand 28, 68 of the PDT device 20, 60 is introduced through a small opening, e.g., a burr hole, or other percutaneous penetration in the patient's cranium, or through natural openings in the patient's head, such as transoral or transphenoidal procedures. The wand is advanced intraluminally and guided to a target site within the brain in a conventional manner, i.e., percutaneously, transluminally or using other minimally invasive or traditional open surgery techniques. The chosen technique may be performed in conjunction with an instrument guiding technology for guiding the PDT device 20, 60 to the target site within the brain. Accordingly, the target site may be charted with a variety of imaging techniques, such as computerized tomography (CT) scanning, magnetic resonance imaging (MRI), ultrasound, angiography, radionucleotide imaging, electroencephalography (EEG) and the like. In conjunction with one of these imaging procedures, typically CT or MRI, the user may also use compatible stereotactic systems for guiding the instrument to the target site. In standard stereotactic systems, a frame, e.g., a Leksell, Todd-Wells or Guiot frame, fixes the head of the patient to the image. These frames, combined with radiological landmarks and a brain atlas, provide anatomical localization to within ±1 mm. Alternatively, imaged guided frameless stereotactic systems that utilize modern imaging, computer software and a locating device, may be employed. For use with these guidance and locating techniques, the wand 28, 68 may have a location marker 21 comprising material which contains a mobile phase suitable for MRI imaging by commercial machines, and which is sufficiently X-Ray-opaque for adequate imaging on CT or X-ray.

Once the distal end of the wand 28, 68 is positioned adjacent to, or in contact with, the affected tissue at the target site, light is delivered via the fiber optic cables 40, 76. A photosensitive compound, such as 5-ALA or Photophrin, is then delivered through the lumen of the shaft or through another catheter to the tissue region. Light is then applied through the apertures 50 in the end cap 44 or from the LED's 80 directly at the desired site in the presence of the photosensitive compound to treat the tissue structure. The light is sufficient for the therapeutic treatment of intracranial tumors while minimizing the collateral damage to surrounding tissue or nerves within the brain of the patient. The power sources can be utilized to illuminate fiber probes or the LED's which emit light at wavelengths of either 405 nm wavelength, for diagnostic purposes, or 635 nm, or therapeutic purposes. It is understood that the delivered light may be at other wavelengths, including within or outside the range of 405 nm to 635 nm The application of light for appropriate time intervals affects or otherwise modifies the target tissue. The light is sufficient to activate the photosensitive compound, which results in death of the tumor tissue. The tissue volume over which the light is delivered may be precisely controlled.

When using the PDT device 60 comprising the plurality of LED's 80, each corresponding fiber optic cable 76 is preferably introduced to the brain through the wand 68 such that a particular LED 80 penetrates to a desired portion of the brain tissue. Such an arrangement allows for inserting the wand 68 through the intervening brain tissue, precisely locating the wand 68 relative to a specific tissue region and then advancing the plurality of LED's via the fiber optic cables 76 for positioning the LED's at a predetermined tissue region for treating the tissue region.

The device for selectively applying photodynamic therapy to structures in the brain has many advantages, including providing a minimally invasive method for delivering light for PDT treatment of tumors in the brain. Placement of means for light delivery at the distal end of the device to brings the light source directly to the desired site providing light irradiation to a defined, targeted area of tissue. The result is precise intracranial treatment within tissue in the brain of a patient. The device and method provide the surgeon the ability to treat malignant brain tumors, even those that are in difficult to reach locations, without a large open surgery. The device provides the potential to deliver light therapy, in a diagnostic or therapeutic fashion, to brain tumors via a very small opening the skull, including for those lesions deemed dangerous to operate on.

Although the device and method for PDT has been shown and described in considerable detail with respect to only a few exemplary embodiments thereof, it should be understood by those skilled in the art that we do not intend to limit the device and method to the embodiments since various modifications, omissions and additions may be made to the disclosed embodiments without materially departing from the novel teachings and advantages, particularly in light of the foregoing teachings. For example, therapeutic use of PDT in the brain is described, but it is understood that PDT for any other part of the body is contemplated. In addition, the choice of materials used in each of the components of the devices described herein, and in particular the overall geometry of the devices, can be specifically tailored to provide the desired properties for a given treatment indication. Accordingly, we intend to cover all such modifications, omission, additions and equivalents as may be included within the spirit and scope of the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A non-implantable surgical apparatus that uses a light source and a power supply for minimally invasive surgical treatment of a tissue region of a brain of a patient, the non-implantable surgical apparatus comprising:

a housing having a proximal and distal end, the housing comprising a handle configured to be grasped and manipulated by a surgeon during a surgical procedure and to remain outside of the patient throughout the surgical procedure; and a wand extending from the distal end of the housing, the wand comprising:

an outer shaft having a proximal end and a distal end for positioning within the tissue region of the brain during the surgical procedure, the outer shaft defining a lumen extending between the proximal end and the distal end of the outer shaft;

an end cap having a closed end in mechanical communication with the distal end of the outer shaft comprising one or more apertures disposed along a longitudinal surface of the end cap and parallel to a longitudinal axis of the end cap;

an inner fiber optic cable having a distal end and a proximal end adapted to be operatively connected to the light source, the fiber optic cable configured to be received within the lumen and extend from the proximal end of the shaft to adjacent the distal end of the shaft;
a diffuser element disposed within the end cap and configured to receive light emitted at the distal end of the inner fiber optic cable;
a ball bearing having a reflective coating disposed at a distal end of the diffuser element and within the end cap, and configured to reflect light received from the diffuser element laterally and proximally through the one or more apertures; and
a piezoelectric ceramic member disposed within the end cap and located distally from the ball bearing, the piezoelectric ceramic member being coupled to wire connectors that extend to the proximal end of the outer shaft where they are adapted to be operatively connected to the power supply,
wherein the piezoelectric ceramic member is adapted to deliver sound waves to the tissue region of the brain during the surgical procedure,
wherein the piezoelectric ceramic member has a cylindrical shape having a cylindrical axis co-axial with a longitudinal axis of the outer shaft lumen, and
wherein the fiber optic cable is adapted to deliver light from the light source via the diffuser element and the ball bearing through the at least one aperture of the end cap to the tissue region of the brain in proximity to the distal end of the outer shaft during the surgical procedure.

2. The non-implantable surgical apparatus as recited in claim 1, wherein the outer shaft comprises a location marker adapted to be located by one of magnetic resonance imaging, computerized x-ray tomography, or combinations thereof.

3. The non-implantable surgical apparatus as recited in claim 1, wherein the housing includes an actuating button and a frequency level adjustment knob that enables adjustment of an intensity of the sound waves.

4. The non-implantable surgical apparatus as recited in claim 1, wherein the housing further includes an indicator light configured to show when the light source is powered.

5. The non-implantable surgical apparatus as recited in claim 1, wherein the end cap has a narrowed distal end terminating in a sealed point, and further comprises a cylindrical cavity co-extensive with the outer shaft lumen.

6. The non-implantable surgical apparatus as recited in claim 5, wherein the diffuser element, the ball bearing, and the piezoelectric ceramic member are disposed within the cylindrical cavity of the end cap.

7. The non-implantable surgical apparatus as recited in claim 1, wherein the one or more apertures comprises multiple apertures disposed circumferentially about a body of the end cap.

8. A method for minimally invasive surgical treatment of a tissue region of a brain of a patient, the minimally invasive surgical treatment method comprising the steps of:
providing a non-implantable irradiating device including a light source and a power supply for selectively irradiating tissue, the irradiating device comprising:
an outer shaft having a proximal end and a distal end for positioning within the tissue region of the brain, the outer shaft defining a lumen extending between the proximal end and the distal end of the outer shaft and having at least one aperture adjacent the distal end of the outer shaft,
an end cap having a closed end in mechanical communication with the distal end of the outer shaft comprising one or more apertures disposed along a longitudinal surface of the end cap and parallel to a longitudinal axis of the end cap,
an inner fiber optic cable having a distal end and a proximal end configured to be operatively connected to the light source, the fiber optic cable configured to be received within the lumen and extend from the proximal end of the outer shaft to adjacent the distal end of the outer shaft,
a diffuser element disposed within the end cap and configured to receive light emitted at the distal end of the inner fiber optic cable,
a ball bearing having a reflective coating disposed at a distal end of the diffuser element and within the end cap, and configured to reflect light received from the diffuser element laterally and proximally through the one or more apertures, and
a piezoelectric ceramic member disposed within the end cap and located distally from the ball bearing, the piezoelectric ceramic member being coupled to wire connectors that extend to the proximal end of the outer shaft where they are adapted to be operatively connected to the power supply, wherein the piezoelectric ceramic member has a cylindrical shape having a cylindrical axis co-axial with a longitudinal axis of the outer shaft lumen;
positioning the distal end of the outer shaft within close proximity to a selected site adjacent the tissue region in the brain during a surgical procedure;
delivering sound waves during the surgical procedure from the piezoelectric ceramic member to the tissue region of the brain;
delivering light during the surgical procedure from the light source through the fiber optic cable and the at least one aperture of end cap to the tissue region of the brain in proximity to the distal end of the outer shaft sufficient to kill a portion of the tissue; and
discontinuing delivery of light and sound waves and removing the irradiating device from the brain of the patient as part of the surgical procedure to conclude the minimally invasive surgical treatment.

9. The minimally invasive surgical treatment method as recited in claim 8, further comprising selectively determining a site within the tissue of the brain for light delivery and sound wave delivery.

10. The minimally invasive surgical treatment method as recited in claim 9, wherein the outer shaft has a location marker, and wherein the selectively determining step comprises locating the position of the location marker within the brain by utilizing magnetic resonance imaging, computerized x-ray tomography, or combinations thereof.

11. The minimally invasive surgical treatment method as recited in claim 9, wherein the selectively determined site is a tumor.

12. The minimally invasive surgical treatment method as recited in claim 8, further comprising delivering photosensitive fluid activated by radiation to the tissue region, and delivering sufficient light to the tissue region in the presence of the photosensitive fluid to kill the tissue.

13. The minimally invasive surgical treatment method as recited in claim 8, wherein the positioning step comprises introducing the outer shaft through a percutaneous penetration in a skull of the patient.

14. The minimally invasive surgical treatment method as recited in claim 8, wherein the irradiating device further comprises a housing having a proximal end and a distal end, and a wand extending from the distal end of the housing, wherein the outer shaft, the inner fiber optic cable, and the piezoelectric ceramic member are part of the wand, and wherein the positioning step includes grasping and manipulating the housing to position the distal end of the outer shaft within close proximity to the selected site, and wherein removing the irradiating device from the brain of the patient includes grasping and manipulating the housing.

15. The minimally invasive surgical treatment method as recited in claim 14, wherein the housing includes a handle, and wherein the positioning step includes grasping and manipulating the handle to position the distal end of the outer shaft within close proximity to the selected site.

16. The minimally invasive surgical treatment method as recited in claim 14, wherein the housing includes an actuating button and a frequency level adjustment knob, and wherein the delivering sound waves step includes adjusting the frequency level adjustment knob to adjust an intensity of the sound waves, and wherein the delivering light step includes actuating the actuating button to deliver light from the light source through the fiber optic cable, the diffuser element, and the ball bearing through the at least one aperture of the outer shaft to the tissue region of the brain in proximity to the distal end of the outer shaft.

17. The minimally invasive surgical treatment method as recited in claim 14, wherein the housing includes an indicator light, and wherein discontinuing delivery of light causes the indicator light to show that the light source is no longer powered.

18. The minimally invasive surgical treatment method as recited in claim 8, wherein the non-implantable irradiating device further comprising an end cap having a narrowed distal end terminating in a sealed point, and a cylindrical cavity co-extensive with the outer shaft lumen.

19. The minimally invasive surgical treatment method as recited in claim 18, wherein the diffuser element, the ball bearing, and the piezoelectric ceramic member are disposed within the cylindrical cavity of the end cap.

20. The minimally invasive surgical treatment method as recited in claim 8, wherein the one or more apertures comprises multiple apertures disposed circumferentially about a body of the end cap.

* * * * *